US005736330A

United States Patent [19]
Fulton

[11] Patent Number: 5,736,330
[45] Date of Patent: Apr. 7, 1998

[54] METHOD AND COMPOSITIONS FOR FLOW CYTOMETRIC DETERMINATION OF DNA SEQUENCES

[75] Inventor: R. Jerrold Fulton, Cedar Hill, Tex.

[73] Assignee: Luminex Corporation, Austin, Tex.

[21] Appl. No.: 542,401

[22] Filed: Oct. 11, 1995

[51] Int. Cl.$^6$ ............... C12P 1/68; C12P 19/34; C12Q 1/70; C07H 21/04
[52] U.S. Cl. ............... 435/6; 435/5; 435/91.2; 435/7.1; 435/7.2; 435/7.9; 435/210; 536/24.3
[58] Field of Search ............... 435/6, 5, 210, 435/91.2, 7.1–7.9; 436/523; 536/24.3, 26.5

[56] References Cited

U.S. PATENT DOCUMENTS

| | | | |
|---|---|---|---|
| 4,661,913 | 4/1987 | Wu et al. | 364/500 |
| 4,665,020 | 5/1987 | Saunders | 435/7 |
| 4,673,288 | 6/1987 | Thomas et al. | 356/72 |
| 4,676,640 | 6/1987 | Briggs | 356/317 |
| 4,710,021 | 12/1987 | von Behrens | 356/72 |
| 4,713,348 | 12/1987 | Ullman | 436/501 |
| 4,767,205 | 8/1988 | Schwartz et al. | 356/71 |
| 4,778,593 | 10/1988 | Yamashita et al. | 209/3.1 |
| 4,833,084 | 5/1989 | Carrico | 435/20.27 |
| 4,857,451 | 8/1989 | Schwartz | 435/7 |
| 4,868,104 | 9/1989 | Kurn et al. | 435/6 |
| 4,884,886 | 12/1989 | Salzman et al. | 356/367 |
| 4,887,721 | 12/1989 | Martin et al. | 209/579 |
| 4,905,169 | 2/1990 | Buican et al. | 364/525 |
| 4,918,004 | 4/1990 | Schwartz | 435/7 |
| 5,028,545 | 7/1991 | Soini | 436/501 |
| 5,093,234 | 3/1992 | Schwartz | 435/7.21 |
| 5,107,422 | 4/1992 | Kamentsky et al. | 364/413.08 |
| 5,109,124 | 4/1992 | Ramachandran et al. | 536/27.27 |
| 5,127,730 | 7/1992 | Brelje et al. | 356/318 |
| 5,149,661 | 9/1992 | Gjerde et al. | 436/178 |
| 5,150,313 | 9/1992 | van den Engh et al. | 364/569 |
| 5,156,810 | 10/1992 | Ribi | 422/82.01 |
| 5,199,576 | 4/1993 | Corio et al. | 209/564 |

(List continued on next page.)

OTHER PUBLICATIONS

Barker et al. Blood 83: 1079–1085 (Feb. 15, 1994).
Bottema et al., "PCR Amplification of Specific Alleles: Rapid Detection of Known Mutations and Polymorphisms," Mutation Research, 288: 93–102 (1993).
Cantarero et al., "The Adsorptive Characteristics of Proteins for Polystyrene and Their Significance in Solid–Phase Immunoassays," Analytical Biochemistry, 105:375–382 (1980).
Colvin et al., "The Covalent Binding of Enzymes and Immunoglobulins to Hydrophilic Microspheres" in Microspheres: Medical and Biological Applications, 1–13, CRC, Boca Raton, FL, 1988. vol. # not applicable.
Fisher, "The Use of Multiple Measurements in Taxonomic Problems," Annals of Eugenics, 7: 179–188 (1936).
Fulwyler et al., "Flow Microsphere Immunoassay for the Quantitative and Simultaneous Detection of Multiple Soluble Analytes," Methods in Cell Biology, 33: 613–629 (1990).
Illum et al., "Attachment of Monoclonal Antibodies to Microspheres," Methods in Enzymology, 112: 67–84 (1985).

(List continued on next page.)

Primary Examiner—Stephanie W. Zitomer
Assistant Examiner—Dianne Rees
Attorney, Agent, or Firm—Arnold, White & Durkee

[57] ABSTRACT

A method for the analysis of DNA sequences and PCR products comprises the steps of constructing an oligonucleotide-labeled bead set, and labeled complementary probe, and exposing the bead set and probe to a DNA fragment or PCR product under hybridizing conditions and analyzing the combined sample/bead set by flow cytometry. Flow cytometric measurements are used to classify beads within an exposed bead set to determine the presence of identical or nonidentical sequences within the test sample. The inventive technology enables the rapid analysis of DNA sequences and detection of point mutations, deletions and/or inversions while also reducing the cost and time for performing genetic assays.

20 Claims, 3 Drawing Sheets

U.S. PATENT DOCUMENTS

| | | | |
|---|---|---|---|
| 5,200,314 | 4/1993 | Urdea et al. | 435/6 |
| 5,204,884 | 4/1993 | Leary et al. | 377/10 |
| 5,219,763 | 6/1993 | Van Hoegaerden | 436/523 |
| 5,224,058 | 6/1993 | Michaels et al. | 364/554 |
| 5,273,881 | 12/1993 | Sena et al. | 425/6 |
| 5,286,452 | 2/1994 | Hansen | 422/73 |
| 5,319,079 | 6/1994 | Reddy et al. | 536/25.32 |
| 5,326,692 | 7/1994 | Brinkley et al. | 435/6 |
| 5,367,474 | 11/1994 | Auer et al. | 364/555 |
| 5,380,663 | 1/1995 | Schwartz et al. | 436/10 |
| 5,385,822 | 1/1995 | Melnicoff et al. | 435/5 |
| 5,393,673 | 2/1995 | Gjerde | 436/171 |
| 5,401,847 | 3/1995 | Glazer et al. | 546/107 |
| 5,403,711 | 4/1995 | Walder et al. | 435/6 |
| 5,405,784 | 4/1995 | Van Hoegaerden | 436/523 |
| 5,408,307 | 4/1995 | Yamamoto et al. | 356/73 |
| 5,413,907 | 5/1995 | Worton et al. | 435/6 |
| 5,429,923 | 7/1995 | Seidman et al. | 435/6 |
| 5,567,627 | 10/1996 | Lehnen | 436/518 |
| 5,606,045 | 2/1997 | Dandiliker et al. | 536/25.32 |

OTHER PUBLICATIONS

Goss et al., "Major Histocompatibility Complex-specific Prolongation of Murine Skin and Cardiac Allograft Survival after In Vivo Depletion of V$\beta^+$ T Cells," The Journal of Experimental Medicine, 177: 35–44 (1993).

Horan et al., "Fluid Phase Particle Fluorescence Analysis: Rheumatoid Factor Specificity Evaluated by Laser Flow Cytophotometry" in Immunoassays in the Clinical Laboratory, 185–198 (Liss 1979) vol. # not applicable.

Lindmo et al., "Immunometric Assay by Flow Cytometry Using Mixtures of Two Particle Types of Different Affinity," Journal of Immunological Methods, 126: 183–189 (1990).

McHugh, "Flow Microsphere Immunoassay for the Quantitative and Simultaneous Detection of Multiple Soluble Analytes," in Methods in Cell Biology, 42 (Part B),:575–595 (Adacemic Press 1994).

McHugh et al., "Microsphere–Based Fluorescence Immunoassays Using Flow Cytometry Instrumentation," in Clinical Flow Cytometry Ed. K. D. Bauer, et al., Williams and Williams, Baltimore, MD, 1993, 535–544. Vol. # not applicable.

McHugh, "Flow Cytometry and the Application of Microsphere–Based Fluorescence Immunoassays," Immunochemica, 5: 1–6 (1991).

Saiki et al., "Genetic Analysis of Amplified DNA with Immobilized Sequence–Specific Oligonucleotide Probes," Proceedings of the National Academy of Sciences of the United States of America, 86: 6230–6234 (1989).

Vener et al., "A Novel Approach to Nonradioactive Hybridization Assay of Nucleic Acids Using Stained Latex Particles," Analytical Biochemistry, 198: 308–311 (1991).

Vlieger et al., "Quantitation of Polymerase Chain Reaction Products by Hybridization–Based Assays with Fluorescent, Colorimetric, or Chemiluminescent Detection," Analytical Biochemistry, 205, 1–7 (1992).

Wilson et al., "A New Microsphere–Based Immunofluoroescence Assay Using Flow Cytometry," Journal of Immunological Methods, 107: 225–230 (1988).

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GCCTACGCCA CCAGCTCCAA CTAC    24

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GCCTACGCCA CAAGCTCCAA CTAC    24

METHOD AND COMPOSITIONS FOR FLOW CYTOMETRIC DETERMINATION OF DNA SEQUENCES

REFERENCES

Commonly owned and co-pending patent application entitled "Multiplexed Analysis of Clinical Specimens Apparatus and Method," Ser. No. 08/540,814, filed 11 Oct. 1995, by Van S. Chandler, R. Jerrold Fulton, and Mark B. Chandler, is hereby incorporated in its entirety by reference.

FIELD OF THE INVENTION

The present invention provides a rapid, extremely sensitive, and reliable method for analysis of DNA sequences by flow cytometry. The invention has wide applicability but is particularly valuable as a method for detecting genetic variations associated with disease, malignancy, or other disorders.

BACKGROUND OF THE INVENTION

Recent advances in genetic analyses have provided a wealth of information regarding specific mutations occurring in particular genes in given disease states. Consequently, use of an individual's genetic information in diagnosis of disease is becoming increasingly prevalent. Genes responsible for disease have been cloned and characterized in a number of cases, and it has been shown that responsible genetic defects may be a gross gene alteration, a small gene alteration, or even in some cases, a point mutation. There are a number of reported examples of diseases caused by genetic mutations. Other uses of DNA analysis, for example in paternity testing, etc., are also important and can be used in accordance with the invention.

Current techniques for genetic analysis have been greatly facilitated by the development and use of polymerase chain reaction (PCR) to amplify selected segments of DNA. The power and sensitivity of the PCR has prompted its application to a wide variety of analytical problems in which detection of DNA or RNA sequences is required.

PCR is capable of amplifying short fragments of DNA, providing short (20 bases or more) nucleotides are supplied as primers. The primers anneal to either end of a span of denatured DNA target and, upon renaturation, enzymes synthesize the intervening complementary sequences by extending the primer along the target strand. During denaturation, the temperature is raised to break apart the target and newly synthesized complementary sequence. Upon cooling, renaturation and annealing, primers bind to the target and the newly made opposite strand and now the primer is extended again creating the complement. The result is that in each cycle of heating and renaturation followed by primer extension, the amount of target sequence is doubled.

One major difficulty with adoption of PCR is the cumbersome nature of the methods of analyzing the reaction's amplified DNA products. Methods for detecting genetic abnormalities and PCR products have been described but they are cumbersome and time consuming. For example, U.S. Pat. No. 5,429,923 issued Jul. 4, 1995 to Seidman, et al., describes a method for detecting mutations in persons having, or suspected of having, hypertrophic cardiomyopathy. That method involves amplifying a DNA sequence suspected of containing the disease associated mutation, combining the amplified product with an RNA probe to produce an RNA-DNA hybrid and detecting the mutation by digesting unhybridized portions of the RNA strand by treating the hybridized product with an RNAse to detect mutations, and then measuring the size of the products of the RNAse reaction to determine whether cleavage of the RNA molecule has occurred.

Other methods used for detecting mutations in DNA sequences, including direct sequencing methods (Maxim and Gilbert, PNAS USA, 74, 560–564, 1977); PCR amplification of specific alleles, PASA (Botttema and Sommer, Muta. Res., 288, 93–102, 1993); and reverse dot blot method (Kawasaki, et al., Methods in Enzymology, 218, 369–81, 993) have been described. These techniques, while useful, are time consuming and cumbersome and for that reason are not readily adaptable to diagnostic assays for use on a large scale.

SUMMARY OF THE INVENTION

The present invention provides a significant advance in the art by providing a rapid and sensitive flow cytometric assay for analysis of genetic sequences that is widely applicable to detection of any of a number of genetic abnormalities. In general, the methods of the present invention employ a competitive hybridization assay using DNA coupled microspheres and fluorescent DNA probes.

In practice of the invention, oligonucleotides from a region of a gene to which a disease associated mutation has been mapped are synthesized and coupled to a microsphere (bead) by standard techniques such as by carbodiimide coupling. A fluorescent oligonucleotide, complementary to the oligonucleotide on the bead, is also synthesized. To perform a test in accordance with the invention, DNA (which is to be tested for a mutation in a gene of interest) is purified and subjected to PCR amplification using standard techniques and PCR initiation probes directed to amplify the particular region of DNA to which such a mutation has been mapped. The PCR product is then incubated with the beads under conditions sufficient to allow hybridization between the amplified DNA and the oligonucleotides present on the beads. A fluorescent DNA probe that is complementary to the oligonucleotide coupled to the beads is also added under competitive hybridization conditions. Aliquots of the beads so reacted are then run through a flow cytometer and the intensity of fluorescence on each bead is measured to detect the level of fluorescence which indicates the presence or absence of mutations in the samples.

For example, when beads labeled with an oligonucleotide probe corresponding to a non-mutated (wild-type) DNA segment are hybridized with the PCR product from an individual who has a non-mutated wild-type DNA sequence in the genetic region of interest, the PCR product will effect a significant competitive displacement of fluorescent oligonucleotide probe from the beads and, therefore, cause a measurable decrease in fluorescence of the beads, e.g., as compared to a control reaction that did not receive PCR reaction product. If, on the other hand, a PCR product from an individual having a mutation in the region of interest is incubated with the beads bearing the wild-type probe, a significantly lesser degree of displacement and resulting decrease in intensity of fluorescence on the beads will be observed because the mutated PCR product will be a less effective competitor for binding to the oligonucleotide coupled to the bead than the perfectly complementary fluorescent wild-type probe. Alternatively, the beads may be coupled to an oligonucleotide corresponding to a mutation known to be associated with a particular disease and similar principles applied. The ratio of reactivity of the PCR product with beadsets bearing the wild type versus known mutant sequences identifies the PCR product as wild-type, known mutant, or unknown mutant. In conjunction with the co-pending application entitled "Multiplexed Analysis of Clinical Specimens Apparatus and Method," by Van S. Chandler, R. Jerrold Fulton and Mark B. Chandler, the reactivity of a PCR product with the wild-type and other known mutations can be analyzed simultaneously. The invention thus provides one with the ability to measure any of a number of genetic variations including point mutations, insertions, deletions, inversions, and alleles in a simple, exquisitely sensitive, and efficient format.

DETAILED DESCRIPTION OF THE PREFERRED EMBODIMENTS

Figure 1A:
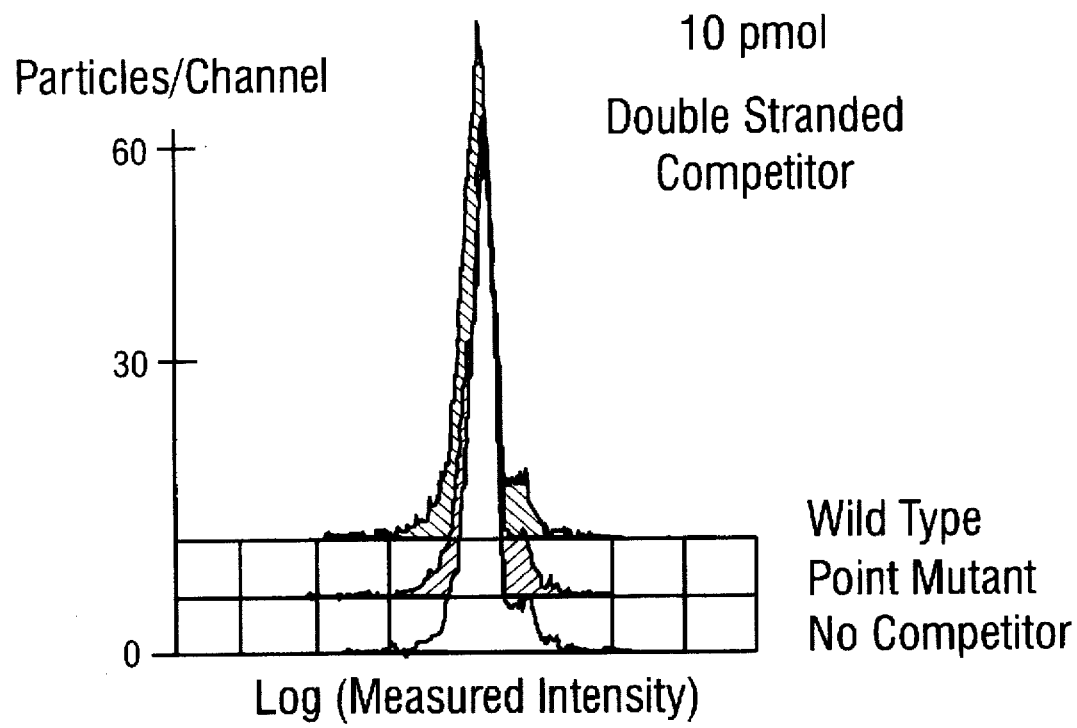
FIGS. 1a through 1c show experimental data for DNA detection using a double stranded competitor and a Wild-Type "B" Oligonucleotide probe.

The present invention has wide-spread advantages for detection of any of a number of mutations of interest in the gertomit DNA of an individual or organism and has the advantages of being both rapid and extremely accurate in effecting the detection of such mutations. The invention will find wide applicability in diagnosis of a number of genetically associated disorders as well as in other applications where identification of genetic mutations may be important. Exemplary diseases include without limitation, diseases such as cystic fibrosis, generalized myotonia and myotonia congenita, hyperkalemic periodic paralysis, hereditary ovalocytosis, hereditary spherocytosis and glucose malabsorption; which are associated with mutations in the genes encoding ion transporters; multiple endocrine neoplasia, which is associated with mutations in the MEN2a, b, and MEN1 genes; familial medullary thyroid carcinoma, and Hirschsprung's disease, which are associated with mutations in the ret proto-oncogene; familial hypercholesterolemia, which is associated with mutations in the LDL receptor gene; neurofibromatosis and tuberous sclerosis, which are associated with mutations in the NF1 gene, and NF type 2 gene; breast and ovarian cancer, which are associated with mutations in the BRCA1, BRCA2, BRCA3 genes; familial adenomatous polyposis, which is associated with mutations in the APC gene; severe combined immunodeficiency, which is associated with mutations in the adenosine deaminase gene; xeroderma pigmentosum, which is associated with mutations in the XPAC gene; Cockayne's syndrome, which is associated with mutations in the ERCC6 excision repair gene; fragile X, which is associated with mutations in the fmrl gene; Duchenne's muscular dystrophy, which is associated with mutations in the Duchenne muscular dystrophy gene; myotonic dystrophy, which is associated with mutations in the myotonic dystrophy protein kinase gene; bulbar muscular dystrophy, which is associated with mutations in the androgen receptor genes; Huntington's disease, which is associated with mutations in the Huntington's gene; Peutz-jegher's syndrome; Lesch-Nyhan syndrome, which is associated with mutations in the HPRT gene; Tay-Sachs disease, which is associated with mutations in the HEXA gene; congenital adrenal hyperplasia, which is associated with mutations in the steroid 21-hydroxylase gene; primary hypertension, which is associated with mutations in the angiotensin gene; hereditary non-polyposis, which is associated with mutations in the hNMLH1 gene; colorectal carcinoma, which is associated with mutations in the 2 mismatch repair genes; colorectal cancer, which is associated with mutations in the APC gene; forms of Alzheimer's disease which have been associated with the apolipoprotein E gene, retinoblastoma, which is associated with mutations in the Rb gene; Li-Fraumeui syndrome, which is associated with mutations in the p53 gene; various malignancies and diseases that are associated with translocations: e.g., in the bcr/abl, bcl-2 gene; chromosomes 11 to 14 and chromosomes 15 to 17 transpositions. The references at the end of the specification which are expressly incorporated herein by reference describe genetic mutations associated with certain diseases which may be tested for in accordance with the invention as well as sequences provided in GENBANK, the contents of which are also expressly incorporated herein by reference.

General Approach

A general approach for detecting a DNA mutation in accordance with this aspect of the invention is as follows. In a first step, a suitable probe for detecting a mutation of interest is selected. In an illustrative embodiment, selected oligonucleotides, representing wild-type and mutant sequences, from a region of a gene known to contain a mutation are prepared. Such oligonucleotides are coupled to microspheres by techniques known in the art, (e.g., carbodiimide coupling, or other means) to produce individual aliquots of beads having known oligonucleotides coupled thereto. The oligonucleotides must be a sufficient length to allow specific hybridization in the assay, e.g., generally between about 10 and 50 nucleotides, more preferably between about 20 and 30 nucleotides in length. In a preferred embodiment, a saturating amount of the oligonucleotide is bound to the bead. Fluorescent oligonucleotides, complementary to all or part of the sequences attached to each bead, are also prepared.

Next, PCR primers are selected which are used to amplify the particular region of DNA in the sample that contains the sequence corresponding to the oligonucleotide coupled to the beads. Either double stranded or single stranded PCR techniques may be used. If double stranded product is produced, the amplified PCR product is made single stranded by heating to a sufficient temperature to and for a sufficient time to denature the DNA (e.g., for about 1 to about 5 minutes at about 90°–95° C. in 2.3X SSC hybridization buffer). The mixture is cooled, and the beads are added and incubated with the PCR product under conditions suitable to allow hybridization to occur between the oligonucleotide on the beads and the PCR product (e.g., at room temperature for about 10 minutes). The fluorescent DNA probe may then be added and the entire mixture incubated under hybridization conditions suitable to allow competitive hybridization to occur (e.g., 5 minutes at 65° C., then cooling to room temperature over a period of several hours in 2.3X SSC buffer). As those of skill in the art will recognize, the concentrations of the PCR product and fluorescent probe to be used may vary and may be adjusted to optimize the reaction.

In general, the concentrations of PCR product and fluorescent probe to be used are adjusted so as to optimize the detectable loss of fluorescence resulting from competitive inhibition without sacrificing the ability of the assay to discriminate between perfect complementarity and one or more nucleotide mismatches. In an exemplary assay, the concentration of PCR product complementary to the oligonucleotide bound to the beads may be on the order of 1 to 10 times the concentration of fluorescent probe used. If the PCR product is much longer than the bead bound oligonucleotide, the amount of PCR product may be increased accordingly to reflect relative molar concentrations in the region of DNA complementary to bead bound oligonucleotide. The fluorescent probe should preferably be added in an amount sufficient to saturate the complementary oligonucleotide on the beads, e.g., in the range of from 1 to 1000 fold and more preferably 2–100 fold or 20–50 fold the concentration of oligonucleotide bound to the bead.

If the PCR product is perfectly complementary to the oligonucleotide on the bead, it will competitively hybridize to it with a higher degree of binding affinity than will be observed if the PCR product is not perfectly complementary. Thus, the PCR product will decrease the binding of the fluorescent complementary oligonucleotide to the bead more or less efficiently depending on the level of complementarity of the PCR product.

The fluorescent oligonucleotide probe may be prepared by methods known in the art such as those described in U.S. Pat. No. 5,403,711, issued Apr. 4, 1995 which is incorporated herein by reference, or by other means well-known in the art.

The reacted sample is analyzed by flow cytometry to determine a change in the fluorescence intensity of the beads. The results are straightforward to analyze for one of ordinary skill. If the sequence that is completely complementary to the nucleotide sequence on the bead of interest is present in the PCR sample and amplified, significant displacement of the fluorescent labeled probe from the bead will be observed. A lesser degree of displacement will be observed if there is a point mutation existent in the PCR product to be measured so that there is less than complete complementarty between the PCR product and the oligonucleotide coupled to the beads. An even lesser degree of diminution of fluorescence will occur if the mutation is more substantial than a point mutation.

A significant advantage of the invention is that it has been shown suitably sensitive to enable the detection of even a single-point mutation. This result makes it extremely desirable and sensitive for use in detecting genotypes where point mutations are associated with disease. The example below describes an application of the invention in an assay directed toward detection of point mutations in the Kras gene, which is associated with a number of malignancies including lung cancer, colon cancer, pancreatic cancer, skin cancer, and the like. The example was performed in accordance with the present invention but is not intended to limit the invention in any way but only to exemplify effectiveness of the invention in detecting disease.

If desired, the inventive method may be adapted for multiplexing as described in our co-pending patent application, filed concurrently with this application, entitled "Multiplexed Analysis of Clinical Specimens Apparatus and Method."

Double Stranded Experiment

Figure 1B:
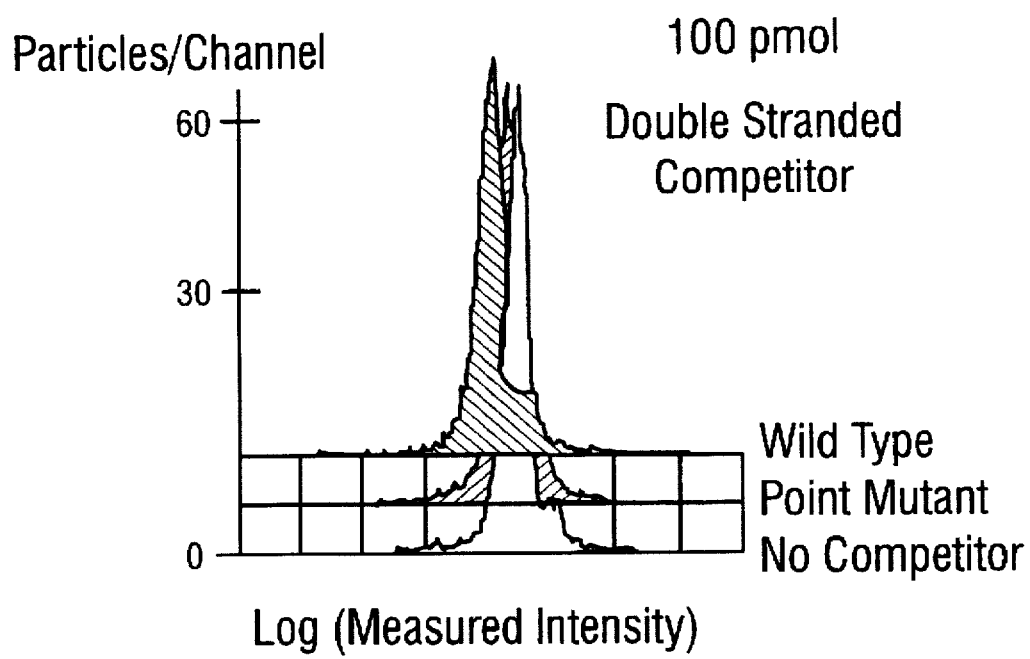
Figure 1C:
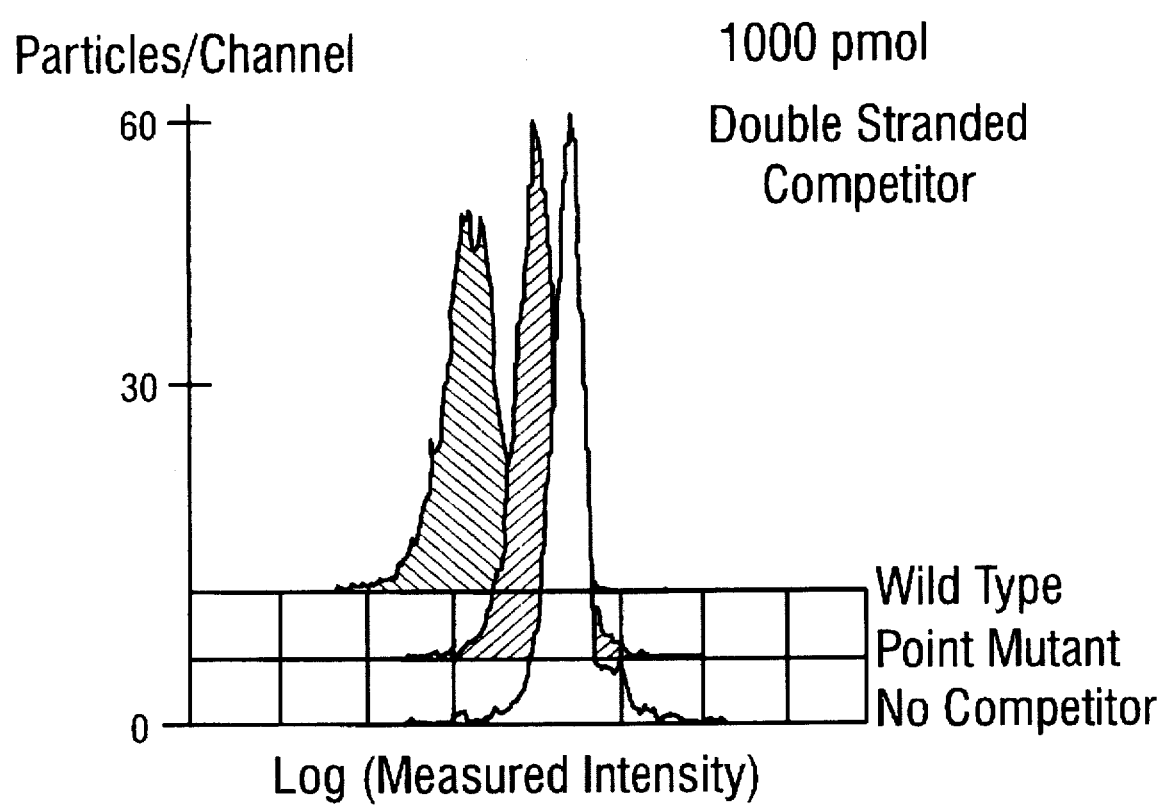

For the purposes of illustration, the two complementary strands of a double-stranded DNA segment are referred to as strand "A" and strand "B". Either strand may be designated "A" or "B". The wild-type "B" strand oligo (ras codon 12) having the oligonucleotide sequence 5'-GCCTACGCCACCAGCTCCAACTAC-3' [SEQ ID No. 1] was coupled to 3.0 micrometers (µm) latex microspheres (manufactured by Interfacial Dynamics) by carbodiimide coupling. Double stranded competitor was prepared by combining equal amounts of both the "A" and "B" strands of either the wild-type or mutant version of the oligo, mutant "B" strand having the sequence 5'-GCCTACGCCAC AAGCTCCAACTAC-3' [SEQ ID No. 2] (ras codon 12) in 5×SSC buffer. Annealing was accomplished by heating the mixture to 65° C. for five minutes, then cooling slowly to room temperature. Competitive hybridization was accomplished by combining approximately 40 picomoles of the bead-attached oligo (wild-type "B" strand) with the indicated mounts of double stranded competitor in 2.3×SSC buffer at approximately 25° C. Finally, 100 picomoles of the fluorescinated oligo (wild-type "A" strand) was added to the reaction mixture. This mixture was incubated for two hours at room temperature, and then diluted with 300 microlitres (µl) of saline pH 7.3, and analyzed on the "FAGSCAN" (manufactured by Becton-Dickinson Immunocytometry Systems). The results are shown in Table 1 below and in FIGS. 1a through 1c.

TABLE 1

| Double-Stranded Experimental Results Using Wild-Type "B" Oligonucleotide | | | |
|---|---|---|---|
| Double Stranded | Percent Inhibition (%) | | Fold Competition |
| Competitor (picomole) | Wild-Type | Mutant | Wild-Type/Mutant |
| 10 | 20 | 9 | 2.2 |
| 100 | 35 | 12 | 2.9 |
| 1000 | 56 | 17 | 3.3 |

Figure 2A:
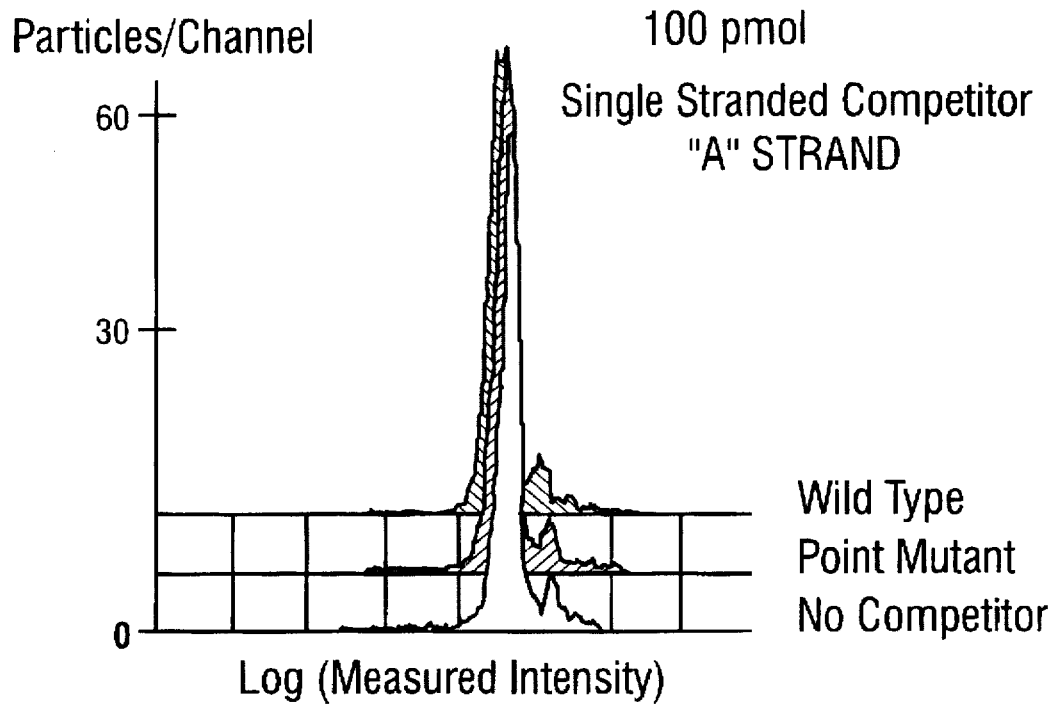
FIGS. 2a and 2b show experimental data for DNA detection using a single stranded competitor and a Wild-Type "B" Oligonucleotide probe.
Figure 2B:
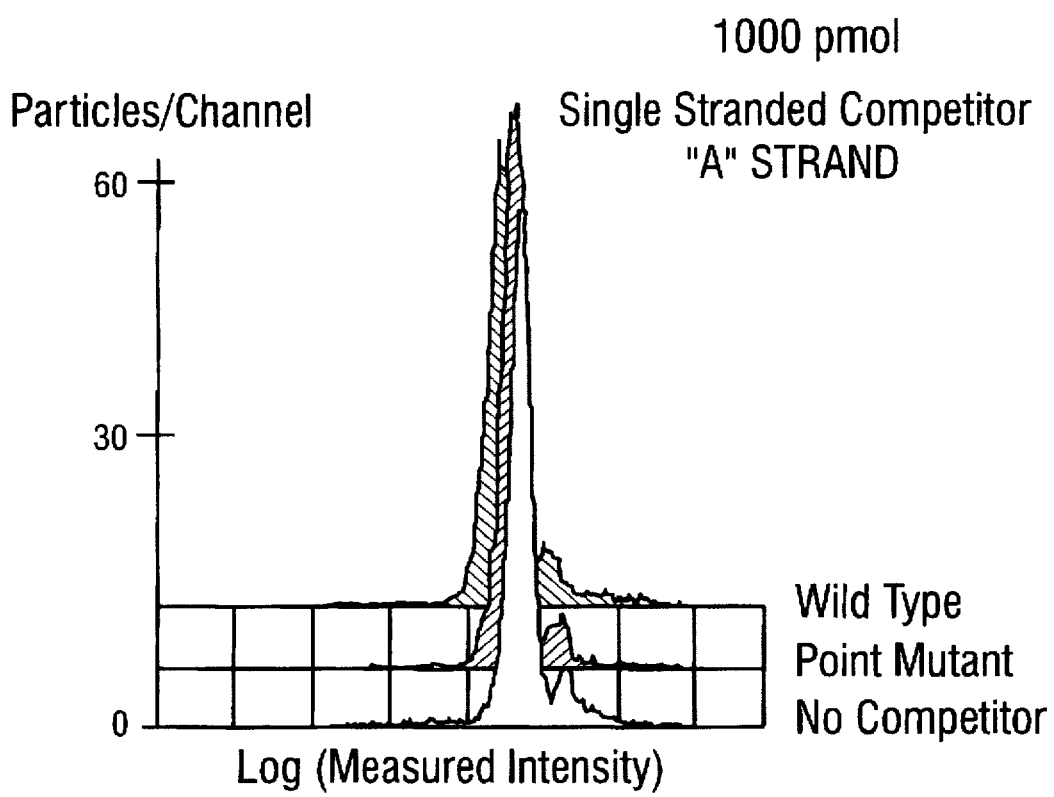

These results (see also FIG. 2) clearly show that the DNA containing the single point mutation ("Mutant") was a detectably less effective inhibitor of hybridization between the DNA on the beads and the fluorescent oligonueleotide probe at all concentrations of competitor tested.

Single Stranded Experiment

The wild-type "B" strand oligo (ras codon 12) was coupled to 3.0 µm latex microspheres (manufactured by Interfacial Dynamics) by carbodiimide coupling. Competitive hybridization was accomplished by combining approximately 40 picomoles of the bead-attached oligo with 100 picomoles of the fluorescinated oligo (wild-type "A" strand) in 2.3×SSC buffer. Finally, the indicated amounts of single stranded competitor (either mutant or wild-type) were added to two separate aliquots of the reaction mixture. These aliquots were incubated for two hours at room temperature, and then diluted with 300 µl of saline pH 7.3, and analyzed on the FACSCAN flow cytometer. The result of these experiments are set forth in Table 2 below and in FIGS. 2a and 2b.

TABLE 2

| Single-Stranded Experimental Results | | | |
|---|---|---|---|
| Single Stranded | Percent Inhibition (%) | | Fold Competition |
| Competitor (picomole) | Wild-Type | Mutant | Wild-Type/Mutant |
| 100 "A" Strand | 14 | 6 | 2.4 |
| 1000 "A" Strand | 25 | 11 | 2.3 |

These results (see also FIGS. 2a and 2b) clearly show that the DNA containing the single point mutation ("Mutant") was a detectably less effective inhibitor of hybridization between the DNA on the beads and the florescent oligonucleotide probe at all concentrations of competitor tested.

The foregoing description of the invention has been directed to particular preferred embodiments in accordance with the requirements of the patent statutes and for purposes of explanation and illustration. It will be apparent, however, to those skilled in the art that many modifications and changes may be made without departing from the scope and the spirit of the a invention. It is apparent that the invention may also be utilized, with suitable modifications within the state of the art. It is the Applicant's intention in the following claims to cover all such equivalent modifications and variations which fall within the true spirit, and scope of the invention.

REFERENCES

1. Human Biology 64: 167–174 (1992) Mutation in Cystic Fibrosis: a Review Spatial Distribution of the DF508. DeBraekeleer, M. and Daigeneault, J.;
2. Science 257: 797–800 (1992) [92358240] The skeletal muscle chloride channel in dominant and recessive human myotonia. M. C. Koch, K. Steinmeyer, C. Lorenz, K. Ricker, F. Wolf, M. Otto, B. Zoll, Lehmann-Horn, K. H. Grzeschik & T. J. Jentsch;
3. Neuron 12: 281–94 (1994) [94153549] Sodium channel mutations in paramyotonia congenita uncouple inactivation from activation. M. Chahine, A. L. George, M. Zhou, S. Ji, W. Sun, R. L. Barchi & R. Horn. Ann Neurol 33: 300–7 (1993) [93270429]; Sodium channel mutations in paramyotonia congenita and hyperkalemic periodic paralysis. L. J. Ptacek, L. Gouw, H. Kwiecinski, P. McManis, J. R. Mendell, R. J. Barohn, A. L. George, R. L. Barchi, M. Robertson & M. F. Leppert;
4. Ann Neurol 33: 300–7 (1993) [93270429] Sodium channel mutations in paramyotonia congenita and hyperkalemic periodic paralysis. L. J. Ptacek, L. Gouw, H. Kwiecinski, P. McManis, J. R. Mendell, R. J. Barohn, A. L. George, R. L. Barchi, M. Robertson & M. F. Leppert. Cell 67: 1021–7 (1991) [92069747] Identification of a mutation in the gene causing hyperkalemic periodic paralysis. L. J. Ptacek, A. L. George, R. C. Griggs, R. Tawil, R. G. Kallen, R. L. Barchi, M. Robertson & M. F. Leppert;
5. Nature 355: 836–8 (1992) [92168137] Defective anion transport activity of the abnormal band 3 in hereditary ovalocytic red blood cells. A. E. Schofield, D. M. Reardon & M. J. Tanner;
6. J Clin Invest 93: 121–30 (1994) [94110314] Duplication of 10 nucleotides in the erythroid band 3 (AE1) gene in a kindred with hereditary spherocytosis and band 3 protein deficiency (band 3PRAGUE). P. Jarolim, H. L. Rubin, S. C. Liu, M. R. Cho, V. Brabec, L. H. Derick, S. J. Yi, S. T. Saad, S. Alper, C. Brugnara et al.;
7. Acta Physiol Scand Suppl 607: 201–7 (1992) [93080072] The Na+/glucose cotransporter (SGLT1). E. M. Wright, E. Turk, K. Hager, L. Lescale-Matys, B. Hirayama, S. Supplisson & D. D. Loo. Nature 350: 354–6 (1991) [91179516]; Glucose/galactose malabsorption caused by a defect in the Na+/glucose cotransporter. E. Turk, B. Zabel, S. Mundlos, J. Dyer & E. M. Wright;
8. Nature 363: 458–60 (1993) [93275414] Germ-line mutations of the RET proto-oncogene in multiple endocrine neoplasia type 2A.L. M. Mulligan, J. B. Kwok, C. S. Healey, M. J. Elsdon, C. Eng, E. Gardner, D. R. Love, S. E. Mole, J. K. Moore, L. Papi, et al.;
9. Nature 367: 375–6 (1994) [94159102] A mutation in the RET proto-oncogene associated with multiple endocrine neoplasia type 2B and sporadic medullary thyroid carcinoma [see comments] R. M. Hofstra, R. M. Landsvater, I. Ceccherini, R. P. Stulp, T. Stelwagen, Y. Luo, B. Pasini, J. W. Hoppener, H. K. van Amstel, G. Romeo, et al.;
10. Nature 367: 378–80 (1994) [94159104] Mutations of the RET proto-oncogene in Hirschsprung's disease [see comments] P. Edery, S. Lyonnet, L. M. Mulligan, A. Pelet, E. Dow, L. Abel, S. Holder, C. Nihoul-Fekete, B. A. Ponder & A. Munnich. Nature 367: 377–8 (1994) [94159103] Point mutations affecting the tyrosine kinase domain of the RET proto-oncogene in Hirschsprung's disease [see comments] G. Romeo, P. Ronchetto, Y. Luo, V. Barone, M. Seri, I. Ceccherini, B. Pasini, R. Bocciardi, M. Lerone, H. Kaariainen, et al.;
11. Hum Mutat 1: 445–66 (1992) [93250847] Molecular genetics of the LDL receptor gene in familial hypercholesterolemia. H. H. Hobbs, M. S. Browri & J. L. Goldstein. Clin Chem 36: 900–3 (1990) [90291682] Use of polymerase chain reaction to detect heterozygous familial hypercholesterolemia. M. Keinanen, J. P. Ojala, E. Helve, K. Aalto-Setala, K. Kontula & P. T. Kovanen;
12. Hum Genet 93: 351–2 (1994) [94171244] Two CA/GT repeat polymorphisms in intron 27 of the human neurofibromatosis (NF1) gene. C. Lazaro, A. Gaona & X. Estivill. Am J Hum Genet 54: 424–36 (1994) [94160989] Deletions spanning the neurofibromatosis 1 gene: identification and phenotype L. M. Kayes, W. Burke, V. M. Riccardi, R. Bennett, P. Ehrlich, A. Rubenstein & K. Stephens. Cell 75: 1305–15 (1993) [94094325] Identification and characterization of the tuberous sclerosis gene on chromosome 16. The European Chromosome 16 Tuberous Sclerosis Consortium;
13. Hum Mol Genet 2: 1823–8 (1993) [94108432] Genetic analysis of the BRCA1 region in a large breast/ovarian family: refinement of the minimal region containing BRCA1. D. P. Kelsell, D. M. Black, D. T. Bishop & N. K. Spurr;
14. Hum Mutat 3: 12–8 (1994) [94163183] Exon eight APC mutations account for a disproportionate number of familial adenomatous polyposis families. D. J. Koorey, G. W. McCaughan, R. J. Trent & N. D. Gallagher. Hum Mutat 1: 467–73 (1992) [93250848] Screening for germ-line mutations in familial adenomatous polyposis patients: 61 new patients and a summary of 150 unrelated patients. H. Nagase, Y. Miyoshi, A. Horii, T. Aoki, G. M. Petersen, B. Vogelstein, E. Maher, M. Ogawa, M. Maruyama, J. Utsunomiya, et al. Cell 66: 589–600 (1991) [91330306] Identification and characterization of the familial adenomatous polyposis coli gene. J. Groden, A. Thliveris, W. Samowitz, M. Carlson, L. Gelbert, H. Albertsen, G. Joslyn, J. Stevens, L. Spirio, M. Robertson, et al.;
15. Hum Mol Genet 2: 1307–8 (1993) [94004878] A missense mutation in exon 4 of the human adenosine deaminase gene causes severe combined immunodeficiency. U. Atasoy, C. J. Norby-Slycord & M. L. Markert. Hum Mol Genet 2: 1099–104 (1993) [94004847] The interleukin-2 receptor gamma chain maps to Xq13.1 and is mutated in X-linked severe combined immunodeficiency, SCIDX1 J. M. Puck, S. M. Deschenes, J. C. Porter, A. S. Dutra, C. J. Brown, H. F. Willard & P.S. Henthom. Cell 73: 147–57 (1993) [93214986] Interleukin-2 receptor gamma chain mutation results in X-linked severe combined immunodeficiency in humans. M. Noguchi, H. Yi, H. M. Rosenblatt, A. H. Filipovich, S. Adelstein, W. S. Modi, O. W. McBride & W. J. Leonard. Am J Med Genet 42: 201–7 (1992) [92125333] Five missense mutations at the adenosine deaminase locus (ADA) detected by altered restriction fragments and their frequency in ADA—patients with severe combined immunodeficiency (ADA-SCID). R. Hirschhorn, A. Ellenbogen & S. Tzall;
16. Mutat Res 273: 193–202 (1992) [92186915] Three nonsense mutations responsible for group A xeroderma pigmentosum. I. Satokata, K. Tanaka, N. Miura, M. Narita, T. Mimaki, Y. Satoh, S. Kondo & Y. Okada J Biol Chem 266: 19786–9 (1991) [92011785] Identification and characterization of xpac protein, the gene product of the human XPAC (xeroderma pigmentosum group A complementing) gene. N. Miura, I. Miyamoto, H. Asiahina, I. Satokata, K. Tanaka & Y. Okada;

17. Nucleic Acids Res 21: 419–26 (1993) [93181229] Structure and expression of the excision repair gene ERCC6, involved in the human disorder Cockayne's syndrome group B. C. Troelstra, W. Hesen, D. Bootsma & J. H. Hoeijmakers; 18. Am J Hum Genet 51: 299–306 (1992) [92351926] A microdeletion of less than 250 kb, including the proximal part of the FMR-I gene and the fragile-X site, in a male with the clinical phenotype of fragile-X syndrome. D. Wohrle, D. Kotzot, M. C. Hirst, A. Manca, B. Korn, A. Schmidt, G. Barbi, H. D. Rott, A. Poustka, K. E. Davies, et al.;

19. Lancet 341: 273–5 (1993) [93148721] Direct diagnosis of carriers of point mutations in Duchenne muscular dystrophy. S. C. Yau, R. G. Roberts, M. Bobrow & C. G. Mathew. Hum Genet 90: 65–70 (1992) [93052247] Molecular genetic analysis of 67 patients with Duchenne/ Becker muscular dystrophy. S. Niemann-Seyde, R. Slomski, F. Rininsland, U. Ellermeyer, J. Kwiatkowska & J. Reiss. Hum Genet 84: 228–32 (1990) [90152651] Rapid detection of deletions in the Duchenne muscular dystrophy gene by PCR amplification of deletion-prone exon sequences. M. Hentemann, J. Reiss, M. Wagner & D. N. Cooper. Nature 322: 73–7 (1986) [86257412] Analysis of deletions in DNA from patients with Becker and Duchenne muscular dystrophy. L. M. Kunkel;

20. Genomics 18: 673–9 (1993) [94140369] Genomic organization and transcriptional units at the myotonic dystrophy locus. D. J. Shaw, M. McCurrach, S. A. Rundle, H. G. Harley, S. R. Crow, R. Sohn, J. P. Thidon, M. G. Hamshere, A. J. Buckler, P. S. Harper, et al. Arch Neurol 50: 1173–9 (1993) [94029649] The myotonic dystrophy gene. A. Pizzuti, D. L. Friedman & C. T. Gaskey. Hum Mol Genet 2: 299–304 (1993) [93271990] Structure and genomic sequence of the myotordc dystrophy (DM kinase) gene. M. S. Mahadevan, C. Amemiya, G. Jansen, L. Sabourin, S. Baird, C. E. Neville, N. Wormskamp, B. Segers, M. Batzer, J. Lamerdin, et al.;

21. Nature 352: 77–9 (1991) [91287825] Androgen receptor gene mutations in X-linked spinal and bulbar muscular atrophy. A. R. La Spada, E. M. Wilson, D. B. Lubalin, A. E. Harding & K. H. Fischbeck. Neurology 42: 2300–2 (1992) [93096171] Strong correlation between the number of CAG repeats in androgen receptor genes and the clinical onset of features of spinal and bulbar muscular atrophy. S. Igarashi, Y. Tanno, O. Onodera, M. Yamazaki, S. Sato, A. Ishikawa, N. Miyatani, M. Nagasla, Y. Ishikawa, K. Sahashi, et al. Science 256: 784–9 (1992) [92271195] Triplet repeat mutations in human disease. C. T. Caskey, A. Pizzuti, Y. H. Fu, R. G. Fenwick & D. L. Nelson;

22. Hum Mol Genet 2: 1713–5 (1993) [94093563] Analysis of the huntingtin gene reveals a trinucleotide-length polymorphism in the region of the gene that contains two CCG-rich stretches and a correlation between decreased age of onset of Huntington's disease and CAG repeat number. D. C. Rubinsztein, D. E. Barton, B.C. Davison & M. A. Ferguson-Smith. Mol Cell Probes 7: 235–9 (1993) [93375991] A new polymerase chain reaction (PCR) assay for the trinucleotide repeat that is unstable and expanded on Huntington's disease chromosomes. J. P. Warner, L. H. Barron & D. J. Brock. Cell 72: 971–83 (1993) [93208892] A novel gene containing a trinucleotide repeat that is expanded and unstable on Huntington's disease chromosomes. The Huntington's Disease Collaborative Research Group;

23. J Clin Invest 83: 11–3 (1989) [89093407] Identification of a single nucleotide change in the hypoxanthine-guanine phosphoribosyltransferase gene (HPRTYale) responsible for Lesch-Nyhan syndrome. S. Fujimori, B. L. Davidson, W. N. Kelley & T. D. Palella. Proc Natl Acad Sci U S A 86: 1919–23 (1989) [89184538] Identification of mutations leading to the Lesch-Nyhan syndrome by automated direct DNA sequencing of in vitro amplified cDNA. R. A. Gibbs, P. N. Nguyen, L. J. McBride, S. M. Koepf & C. T. Caskey. Genomics 7: 235–44 (1990) [90269813] Multiplex DNA deletion detection and exon sequencing of the hypoxanthine phosphoribosyltransferase gene in Lesch-Nyhan families. R. A. Gibbs, P. N. Nguyen, A. Edwards, A. B. Civitello & C. T. Caskey;

24. Nature 333: 85–6 (1988) [88202110] Identification of an altered splice site in Ashkenazi Tay-Sachs disease. E. Arpaia, A. Dumbrille-Ross, T. Maler, K. Neote, M. Tropak, C. Troxel, J. L. Stirling, J. S. Pitts, B. Bapat, A. M. Lamhonwah, et al. J Biol Chem 263: 18587–9 (1988) [89066640] The major defect in Ashkenazi Jews with Tay-Sachs disease is an insertion in the gene for the alpha-chain of beta-hexosaminidase. R. Myerowitz & F. C. Costigan: Hum Mutat 1: 303–9 (1992) [93250824].A mutation common in non-Jewish Tay-Sachs disease: frequency and RNA studies. B. R. Akerman, J. Zielenski, B. L. Triggs-Raine, E. M. Prence, M. R. Natowicz, J. S. Lim-Steele, M. M. Kaback, E. H. Mules, G. H. Thomas, J. T. Clarke, et al.;

25. Clin Endocrinol (Oxf) 38: 421–5 (1993) [93306853] Prenatal diagnosis of congenital adrenal hyperplasia by direct detection of mutations in the steroid 21-hydroxylase gene. G. Rumsby, J. W. Honour & C. Rodeck. Proc Natl Acad Sci U S A 90: 4552–6 (1993) [93281617] Mutations in the CYP11B1 gene causing congenital adrenal hyperplasia and hypertension cluster in exons 6, 7, and 8. K. M. Curnow, L. Slutsker, J. Vitek, T. Cole, P. W. Speiser, M. I. New, P. C. White & L. Pascoe. Hum Genet 89: 109–10 (1992) [92250001] Prenatal diagnosis of 21-hydroxylase deficiency congenital adrenal hyperplasia using the polymerase chain reaction. D. Owerbach, M. B. Draznin, R. J. Carpenter & F. Greenberg;

26. Nucleic Acids Res 20: 1433 (1992) [92220641] PCR detection of the insertion/deletion polymorphism of the human angiotensin converting enzyme gene (DCP1) (dipeptidyl carboxypeptidase 1). B. Rigat, C. Hubert, P. Corvol & F. Soubrier. Biochem Biophys Res Commun 184: 9–15 (1992) [9223 1988] Association of a polymorphism of the angiotensin I-converting enzyme gene with essential hypertension. R. Y. Zee, Y. K. Lou, L. R. Griffiths & B. J. Morris;

27. Nature 368: 258–61 (1994) [94195398] Mutation in the DNA mismatch repair gene homologue hMLH1 is associated with hereditary non-polyposis colon cancer. C. E. Bronner, S. M. Baker, P. T. Morrison, G. Warren, L. G. Smith, M. K. Lescoe, M. Kane, C. Earabino, J. Lipford, A. Lindblom, et al. Oncogene 9: 991–4 (1994) [94151027] DNA alterations in cells from hereditary non-polyposis colorectal cancer patients. C. Wu, Y. Akiyama, K. Imai, S. Miyake, H. Nagasaki, M. Oto, S. Okabe, T. Iwama, K. Mitamura, H. Masumitsu, et al.;

28. Science 263: 1625–9 (1994) [94174309] Mutation of a mutL homolog in hereditary colon cancer [see comments]

N. Papadopoulos, N. C. Nicolaides, Y. F. Wei, S. M. Ruben, K. C. Carter, C. A. Rosen, W. A. Haseltine, R. D. Fleischmann, C. M. Fraser, M. D. Adams, et al. Cell 75: 1215–25 (1993) [94084796] Mutations of a mutS homolog in hereditary nonpolyposis colorectal cancer. F. S. Leach, N. C. Nicolaides, N. Papadopoulos, B. Liu, J. Jen, R. Parsons, P. Peltomaki, P. Sistorten, L. A. Aaltonen, M. Nystrom-Lahti;

29. Hum Mutat 3: 12–8 (1994) [94163183] Exon eight APC mutations account for a disproportionate number of familial adenomatous polyposis families. D. J. Koorey, G. W. McCaughan, R. J. Trent & N. D. Gallagher. Hum Murat 2: 478–84 (1993) [94154735] Simple, rapid, and accurate determination of deletion mutations by automated DNA sequencing of heteroduplex fragments of the adenomatous polyposis coli (APC) gene generated by PCR amplification. K. Tamura, Y. Yamamoto, Y. Saeki, J. Furuyama & J. Utsunomiya;

30. Biochim Biophys Acta 1155: 43–61 (1993) [93277907] Molecular characterization of the retinoblastoma susceptibility gene. D. W. Goodrich & W. H. Lee. Onadim, Z., Hogg, A. & Cowell, J. K. (1993). Mechanisms of ontogenesis in patients with familial retinoblastoma. Br. J. Cancer 68, 958–64;

31. Cancer Res 54: 1298–304 (1994) [94163623] Prevalence and diversity of constitutional mutations in the p53 gene among 21 Li-Fraumeni families. J. M. Birch, A. L. Hartley, K. J. Tricker, J. Prosser, A. Condie, A. M. Kelsey, M. Harris, P. H. Jones, A. Binchy, D. Crowther, et al.;

32. Leukemia 8: 186–9 (1994) [94118546] An optimized multiplex polymerase chain reaction (PCR) for detection of BCR-ABL fusion mRNAs in haematological disorders. N. C. Cross, J. V. Melo, L. Feng & J. M. Goldman. Blood 69: 971–3 (1987) [87129392] bcr-abl RNA in patients with chronic myelogenous leukemia. E. Shtivelman, R. P. Gale, O. Dreazen, A. Berrebi, R. Zaizov, I. Kubonishi, I. Miyoshi & E. Canaani bcl-2; Diagn Mol Pathol 2: 241–7 (1993) [94163382] Rearrangement of the BCL-2 gene in follicular lymphoma. Detection by PCR in both fresh and fixed tissue samples. J. Liu, R. M. Johnson & S. T. Traweek. Blood 83: 1079–85 (1994) [94154269] Cytometric detection of DNA amplified with fluorescent primers: applications to analysis of clonal bcl-2 and IgH gene rearrangements in malignant lymphomas. R. L. Barker, C. A. Worth & S. C. Peiper. Br J Cancer 67: 922–5 (1993) [93264208] Detection of bcl-2/JH rearrangement in follicular and diffuse lymphoma: concordant results of peripheral blood and bone marrow analysis at diagnosis. R. Yuan, P. Dowling, E. Zucca, H. Diggelmann & F. Cavalli;

33. Molecular Cloning: A Laboratory Manual, 2d Ed., Cold Spring Harbor Laboratory Press (1989). Sambrook, J., Friteh, E., and Maniails, T.; and 34. PNAS USA 74: 5463–5467 (1977), DNA Sequencing with Chain Terminating Inhibitors, Sanger et al.

What is claimed is:

1. A method for flow cytometric analysis to detect a genetic mutation in a PCR product amplified from a nucleic acid sample containing a target gene of interest, said method comprising the steps of:

(a) obtaining beads coupled to an oligonucleotide molecule, said oligonucleotide molecule including a polymorphic site, said polymorphic site including said genetic mutation or the wild type sequence found at the analogous position of said genetic mutation in a wild type target gene;

(b) forming a mixture by mixing said beads, said PCR product, and a fluorescently labeled nucleic acid probe, said fluorescently labeled nucleic acid probe being:

(i) complementary to said oligonucleotide molecule; and (ii) capable of being competitively inhibited from binding to said oligonucleotide molecule by said PCR product;

(c) forming a reacted sample by incubating said mixture under conditions wherein if said PCR product includes said polymorphic site, said PCR product competitively inhibits binding of said fluorescently labeled nueleic acid probe to said oligonucleotide molecule;

(d) analyzing said reacted sample by flow cytometry to determine the fluorescence of each bead analyzed; and (e) detecting the genetic mutation or absence thereof as a result of the degree of fluorescence on the beads.

2. A method of detecting a genetic mutation in a PCR product amplified from a nucleic acid sample containing a target gene of interest, said method comprising the steps of:

(a) selecting an oligonucleotide probe, said oligonucleotide probe including a polymorphic site, said polymorphic site including said genetic mutation or the wild type sequence found at the analogous position of said genetic mutation in a wild type target gene;

(b) preparing a fluorescent nueleic acid probe complementary to said oligonucleotide probe;

(c) coupling said oligonucleotide probe to cash one of a plurality of beads to form a bead aliquot;

(d) selecting PCR primers to amplify a region of said target gene including said polymorphic site;

(e) amplifying said region of said target gene by PCR to form PCR products;

(f) mixing said bead aliquot, said PCR products and said fluorescent nucleic acid probe to form a mixture;

(g) incubating said mixture under competitive hybridization conditions, wherein if said PCR products include said polymorphic site, said PCR products competitively inhibit binding of said fluorescent nucleic acid probe to said oligonucleotide probe;

(h) measuring the fluorescence of said beads by flow cytometry; and (i) detecting said genetic mutation, or absence thereof, as a function of the measured fluorescence of said beads.

3. The method of claim 1 or 2 wherein said genetic mutation is selected from the group consisting of mutations in multiple endocrine neoplasia type 2a (MEN2a), multiple endocrine neoplasia type 2b (MEN2b), multiple endocrine neoplasia type 1 (MEN 1), ret proto-oncogene, low density lipoprotein (LDL) receptor, neurofibromatosis type 1 (NF1), neurofibromatosis type 2 (NF type 2), breast and ovarian cancer susceptibility type 1 (BRCA1), breast and ovarian cancer susceptibility type 2 (BRCA2), breast and ovarian cancer susceptibility type 3 (BRCA3), adenomatous polyposis coli (APC), adenosine deaminase, Xeroderma Pigmentosum group A correcting (XPAC), excision repair cross complementing rodent repair deficiency complementation group 6 (ERCC6), fragile X mental retardation protein 1 (fmr1), Duchenne muscular dystrophy gene, myotonic dystrophy protein kinase, androgen receptor, Huntington's, hypoxanthine-guanine phosphoribotransferase (HPRT), apolipoprotein E, beta-hexosaminidase alpha chain (HEX A), steroid 2-hydroxyluse, angiotensin, human nodular mixed lymphocytic and histiocytic cell mismatch repair (hNMLH1, 2), retinoblastoma susceptibility (Rb), transformation-associated protein 53 (p53), breakpoint cluster region/tyrosine-protein kinase (bcr/abl), B-cell leukemia/lymphoma 2 (bcl-2), and genes encoding ion transporters.

4. The method of claim 2 wherein said oligonucleotide probe has a length of between 5 and 500 nucleotides.

5. The method of claim 1 or 2 wherein said PCR primers effect amplification of a region of said target nucleic acid sequence identical in length to said oligonueleotide probe in a PCR process.

6. A kit for detection of a genetic mutation in a sample of nueleic acid, said kit comprising:

(a) a first container containing beads coupled to an oligonucleotide capable of specifically hybridizing with a selected PCR product of interest;

(b) a second container containing a PCR primer which effects amplification of a section of nucleic acid complementary to said oligonucleotide in a PCR process; and (c) a third container containing a fluorescent labeled nucleic acid probe which selectively hybridizes to said oligonucleotide.

7. The kit of claim 6, wherein said genetic mutation is selected from the group consisting of mutations in multiple endocrine neoplasia type 2a (MEN2a), multiple endocrine neoplasia type 2b (MEN2b), multiple endocrine neoplasia type 1 (MEN1), ret proto-oncogene, low density lipoprotein (LDL) receptor, neurofibromatosis type 1 (NF1), neurofibromatosis type 2 (NF type 2), breast and ovarian cancer susceptibility type 1 (BRCA1), breast and ovarian cancer susceptibility type 2 (BRCA2), breast and ovarian cancer susceptibilky type 3 (BRCA3), adenomatous polyposis coli (APC), adenosine deaminase, Xeroderma Pigmentosum group A correcting (XPAC), excision repair cross complementing rodent repair deficiency complementation group 6 (ERCC6), fragile X mental retardation protein 1 (fmr1), Duchenne muscular dystrophy gene, myotionic dystrophy protein kinase, androgen receptor, Huntington's, hypoxanthine-guanine phosphoribotransferase (HPRT), apolipoprotein E, beta-hexosaminidase alpha chain (HEXA), steroid 2-hydroxylase, angiotensin, human nodular mixed lymphocytic and histiocytic cell mismatch repair (hNMLH1, 2), retinoblastoma susceptibility (Rb), transformation-associated protein 53 (p53), breakpoint cluster region/tyrosine-protein kinase (bcr/abl), B-cell leukemia/lymphoma 2 (bcl-2), and genes encoding ion transporters.

8. The kit of claim 6 wherein said fluorescent labeled nucleic acid probe has a length of between 5 and 500 nucleotides.

9. The method of claims 1 or 2 wherein said genetic mutation is a translocation or transposition.

10. The method of claim 9, wherein said transposition is the breakpoint cluster region/tyrosine-protein kinase (bcr/abl) chromosomes 11 to 14 gene transposition.

11. The method of claim 9, wherein said transposition is the B-cell leukemia/lymphoma 2 (bcl-2) chromosomes 15 to 17 gene transposition.

12. The kit of claim 6, wherein said genetic mutation is a translocation or transposition.

13. The kit of claim 12, wherein said transposition is the breakpoint cluster region/tryrosine-protein kinase (bcr/abl) chromosomes 11 to 14 gene transposition.

14. The kit of claim 12, wherein said transposition is the B-cell leukemia/lymphoma 2 (bcl-2) chromosomes 15 to 17 gene transposition.

15. A kit for detection of a genetic mutation in a sample of nucleic acid, said kit comprising:

(a) a first container containing beads coupled to an oligonucleotide capable of specifically hybridizing with a selected PCR product of interest; and (b) a second container containing a fluorescent labeled nucleic acid probe which is fully complementary to said oligonucleotide.

16. The kit of claim 15, wherein said genetic mutation is selected from the group consisting of mutations in multiple endocrine neoplasia type 2a (MEN2a), multiple endocrine neoplasia type 2b (MEN2b), multiple endocrine neoplasia type 1 (MEN1), ret proto-oncogene, low density lipoprotein (LDL) receptor, neurofibromatosis type 1 (NF 1), neurofibromatosis type 2 (NF type 2), breast and ovarian cancer susceptibility type 1 (BRCA1), breast and ovarian cancer susceptibility type 2 (BRCA2), breast and ovarian cancer susceptibility type 3 (BRCA3), adenomatous polyposis coli (APC), adenosine deaminase, Xeroderma Pigmentosum group A correcting (XPAC), excision repair cross complementing rodent repair deficiency complementation group 6 (ERCC6), fragile X mental retardation protein 1 (fmr1), Duchenne muscular dystrophy gene, myotionic dystrophy protein kinase, androgen receptor, Huntington's, hypoxanthine-guanine phosphoribotransferase (HPRT), apolipoprotein E, beta-hexosaminidase alpha chain (HEXA), steroid 2-hydroxylase, angiotensin, human nodular mixed lymphocytic and histiocytic cell mismatch repair (hNMLH1,2), retinoblastoma susceptibility (Rb), transformation-associated protein 53 (p53), transformation-associated protein 53 (p53), breakpoint cluster region/tyrosine-protein kinase (bcr/abl), B-cell leukemia/lymphoma 2 (bcl-2), and genes encoding ion transporters.

17. The kit of claim 15, wherein said fluorescent labeled nucleic acid probe has a length of between 5 and 500 nucleotides.

18. The kit of claim 15, wherein said genetic mutation is a translocation or transposition.

19. The kit of claim 18, wherein said transposition is the breakpoint cluster region/tyrosine-protein kinase (bcr/abl) chromosomes 11 to 14 gene transposition.

20. The kit of claim 18, wherein said transposition is the B-cell leukemia/lymphoma 2 (bcl-2) chromosomes 15 to 17 gene transposition.

* * * * *